United States Patent [19]
Barsotti

[11] Patent Number: 5,900,044
[45] Date of Patent: May 4, 1999

[54] ORGANIC SEPARATION FROM HF

[75] Inventor: Domenic Joseph Barsotti, Vineland, N.J.

[73] Assignee: E. I. du Pont de Nemours and Company, Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 08/852,305

[22] Filed: May 7, 1997

Related U.S. Application Data

[63] Continuation of application No. 08/710,041, Sep. 11, 1987, abandoned, which is a continuation of application No. 08/402,785, Mar. 13, 1995, abandoned, which is a continuation-in-part of application No. 08/279,618, Jul. 25, 1994, Pat. No. 5,458,674, which is a continuation of application No. 08/109,372, Aug. 24, 1993, abandoned.

[51] Int. Cl.$^6$ .................................................. B01D 53/04
[52] U.S. Cl. ................................................. 95/131; 95/148
[58] Field of Search ............................. 95/116, 131, 142, 95/148

[56] References Cited

U.S. PATENT DOCUMENTS

| | | |
|---|---|---|
| 3,282,875 | 11/1966 | Connolly et al. . |
| 3,718,627 | 2/1973 | Grot . |
| 3,721,066 | 3/1973 | Teller ......................................... 95/131 |
| 3,727,379 | 4/1973 | Bijleveld et al. ...................... 95/142 X |
| 3,873,629 | 3/1975 | Jones ........................................ 260/653 |
| 3,943,229 | 3/1976 | Keener et al. ........................ 95/131 X |
| 3,947,558 | 3/1976 | Eijl ............................................ 423/483 |
| 3,976,447 | 8/1976 | Merchant et al. ......................... 95/131 |
| 4,157,376 | 6/1979 | Vulikh et al. ........................ 95/131 X |
| 4,329,435 | 5/1982 | Kimoto et al. ............................. 521/38 |
| 4,662,296 | 5/1987 | Grote et al. .............................. 260/413 |
| 4,956,095 | 9/1990 | Robeson et al. ...................... 95/142 X |
| 5,166,114 | 11/1992 | An-hsiang ................................ 502/117 |
| 5,196,616 | 3/1993 | Lee et al. ................................. 570/178 |

FOREIGN PATENT DOCUMENTS

| | | |
|---|---|---|
| 55-109201 | 8/1980 | Japan ....................................... 95/131 |
| 1757721 | 8/1992 | U.S.S.R. .................................. 95/131 |

*Primary Examiner*—Robert Spitzer
*Attorney, Agent, or Firm*—James E. Shipley

[57] ABSTRACT

A process is disclosed for separating HF from organics by passing a mixture of HF and organics through a column or bed containing a polymer which sorbs the HF leaving an essentially pure organic stream. The HF may be recovered from the polymer, or the organics may be recovered with reduced HF concentration. The HF and organics may form an azeotropic or azeotrope-like mixture.

9 Claims, No Drawings

ORGANIC SEPARATION FROM HF

CROSS REFERENCE TO RELATED APPLICATIONS

This application is a continuation of application Ser. No. 08/710,041 filed 11 Sep. 1997, now abandoned, which is a continuation of application Ser. No. 08/402,785 filed Mar. 13, 1995, now abandoned, which is a continuation-in-part of application Ser. No. 08/279,618 filed Jul. 25, 1994, now U.S. Pat. No. 5,485,674, which is a continuation of application Ser. No. 08/109,372 filed Aug. 24, 1993, now abandoned.

BACKGROUND OF THE INVENTION

This invention relates to the field of separating hydrogen fluoride (HF) from organics.

A majority of fluorochemicals of commercial interest, including chlorofluorocarbons (CFC's), hydrogen-containing chlorofluorocarbons (HCFC's), hydrogen-containing fluorocarbons (HFC's) and perfluorocarbons (FC's), are manufactured by using halogen-exchange reactions. Generally, in these reactions, the appropriate chlorocarbon is reacted with a fluorine-containing compound which serves as the fluorine source. Usually, the fluorine source is HF and it is used in the presence of various catalytic compounds. This halogen-exchange reaction may be illustrated by considering the preparation of monochlorodifluoromethane (HCFC-22); in this illustration, chloroform is the chlorocarbon employed and HF is the fluorine source.

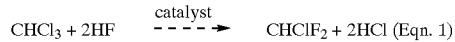

$$CHCl_3 + 2HF \xrightarrow{\text{catalyst}} CHClF_2 + 2HCl \quad \text{(Eqn. 1)}$$

The catalysts that are useful in this reaction include various metal oxides and halides and the reaction can be carried out in either vapor or liquid phase. The amount of HF which is used in the above illustrated reaction is almost always in excess of the stoichiometric amount and may be present in as much as a ten-fold excess. Excess HF is used to increase yields and conversions and to reduce the reaction time. In the reaction illustrated by Equation(1), the crude reaction stream may contain some unreacted $CHCl_3$, under-fluorinated $CHCl_2F$, the desired $CHClF_2$, by-product hydrogen chloride (HCl) and unreacted HF. By the use of a combination of art-known processes, such as distillation, phase separation and the like, HCl can be recovered as useful anhydrous HCl, $CHCl_3$ and $CHCl_2F$ can be recovered, and most of the HF can be recovered. The $CHCl_3$, $CHCl_2F$ and the HF may then be used for other purposes or recycled. However, the desired product, $CHClF_2$ (HCFC-22), cannot be recovered by distillation completely free of HF because HCFC-22 and HF form an azeotropic mixture and such mixtures are not amenable to separation by ordinary distillation.

An object of the present invention is to provide an effective, economical, and easily installed process for separating HF from organics, including the separation of HF and organics which form azeotropic or azeotrope-like mixtures. Another object of the present invention is to provide a process for separating and recovering the components of a mixture of HF and an organic composition so that waste product disposal problems/costs are avoided and/or reduced. Another object is to provide a process for recovering HF in substantially anhydrous form which may be directly recycled as a process reactant. Another object is to provide a process which avoids the necessity of deacidifying mixtures containing HF using aquious scrubbing techniques which can cause the formation of unwanted impurities. A further object is to provide a separation process for a mixture of HF and organics which results in obtaining the individual components of the mixture in essentially pure forms.

These and other objects of the invention will be clear from the description of the invention provided herein.

SUMMARY OF THE INVENTION

A process has been discovered for separating HF from organics comprising
   providing a polymer capable of selective sorption of HF,
   contacting a mixture of HF and organics with the polymer,
   isolating the polymer containing sorbed HF and, thereafter,
   recovering the sorbed HF from the polymer.

In addition, a process has been discovered for separating HF from organics comprising
   providing a polymer capable of selective sorption of HF,
   contacting a mixture of HF and organics with the polymer and, thereafter,
   recovering the organics with reduced HF concentration.

The mixture of HF and organics can be either nonazeotropic, azeotropic or azeotrope-like.

DESCRIPTION OF THE PREFERRED EMBODIMENT

In the present invention, by sorption is meant either adsorption or absorption or a combination of both.

In the present invention, by organic is meant any hydrocarbon or derivative of a hydrocarbon, straight chain or cyclic, in liquid or gaseous form, which is capable of forming intimate mixtures with HF. This includes, but is not limited to, halocarbons such as chlorofluorocarbons, hydrogen-containing chlorofluorocarbons, perfluorocarbons, and hydrogen containing fluorinated hydrocarbons.

As is known, an azeotrope is a mixture of two or more components wherein, at constant pressure, the liquid phase and the vapor phase above the liquid phase have identical compositions at the boiling point of the liquid; thus, the components cannot be separated by conventional distillation. In the context of the present invention, an azeotrope-like mixture is a mixture which is not a true azeotrope but which behaves similarly to an azeotrope, i.e., the mixture boils with little or no change in the vapor and liquid compositions because of the closeness of the boiling points of the components in the mixture or due to some other reasons.

The compositions capable of being separated by the present invention are any mixture of hydrogen fluoride and organics and include azeotropes and azeotrope-like compositions which are difficult to separate into pure components by ordinary distillation. These mixtures may be mixtures of HF with halocarbons such as monochlorodifluoromethane, monochlorotetrafluoroethane, pentafluoroethane and tetrafluoroethane. The mixtures may be either aqueous or nonaqueous mixtures.

The polymer, which is useful in this invention, may be any hydrogen fluoride-resistant polymeric material which is capable of sorbing HF; the polymeric material may be either porous or nonporous. Although the physical form of the polymer is not critical, generally, the forms which are preferred are those which can be handled easily such as granular, beaded, pellet, rolled/coiled sheet, block, spiral or similar forms.

For a polymer to be resistant to degradation upon prolonged contact with HF, it is preferred that the polymers be fluorinated polymers, such as fluorinated ethylene-propylene copolymers, poly (ethylenechlorotrifluoroethylene), poly (chlorotrifluoroethylene), poly (tetrafluoroethylene) copolymers of ethylene and tetrafluoroethylene, poly (vinylidene fluoride) and the like. Also preferred polymers are fluorinated polymers containing inorganic groups such as carboxyl or sulfonyl as described in U.S. Pat. Nos. 3,282,875; 3,718,627 and 4,329,435, incorporated herein by reference. The Nafion® fluorinated polymers (available from DuPont) which contain a sulfonic acid group are particularly preferred. Nafion® is reported to have the structure containing the following recurring units:

and

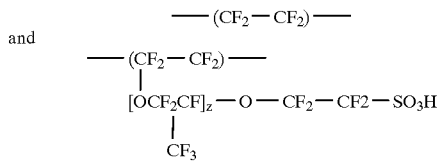

where z is an integer of 1 or greater. These Nafion® polymers have high sorption rates for HF and, at the same time, are highly resistant to degradation by HF.

The instant process provides a means for separating a mixture of organics and HF in either/both gas and/or liquid form. The contacting of the HF and organics with the polymer can be conducted in any vessel capable of containing the HF, organics and polymer. The HF/organic mixture may be run through a closed column or bed which may be filled with polymer in beaded or other similar form.

The amount of HF that can be sorbed by the polymer will vary depending on the type of polymeric material used. When Nafion® polymer is used, sorption of HF in an amount of about 10–15% of the weight of the polymer may be possible before the polymer needs to be regenerated. Isolation of the polymer prior to regeneration may be accomplished in any convenient manner. For example, isolation may be easily accomplished by stopping the flow of the HF/organic feed and draining the residual mixture from the vessel in which it is contained. To enhance the separation of HF from the polymer, i.e., regeneration of the polymer, a vacuum may be used or nitrogen gas can be passed over the polymer to pick-up sorbed HF from the polymer. Regeneration may be accomplished with or without heating to remove the HF from the polymer. Preferably, a heated nitrogen gas back flow can be used and essentially 100% recovery of the HF sorbed by the polymer may be achieved. Once regenerated, the polymer normally is reused in the process.

EXAMPLE 1

A liquid mixture of 0.91 wt. % HF in HCFC-22 was passed through a column (9 mm internal diameter (ID) by 580 mm length) packed with Nafion® polymer (NR-50) beads (2 mm diameter by .5 mm length). During the experiment, the pressure was held constant at 130 psig (748cm Hg) and the temperature was maintained at 23° C. The flow rate was varied from 40 mL/min to 220 mL/min. Flow rates were held constant for periods varying from 30 minutes to 6 hours during which time the fluoride content was continuously monitored. The column effluent contained a maximum of 7 ppm HF as measured by the use of a selective ion electrode in an acetate buffer. In addition, regeneration of the polymer allowed essentially 100% HF recovery using heated nitrogen back flow.

EXAMPLE 2

A vapor mixture of 0.22 wt. % HF, 53.8 wt. % HCFC-124 and 46 wt. % HFC-134a was passed through the Nafion® (NR-50) polymer packed column described in Example 1. During this run the pressure was maintained at 50 psig (334 cm Hg), temperature at 23° C. and flow constant at 150 mL/min. The column effluent contained a maximum 1 ppm HF as determined by the use of a specific ion electrode in an acetate buffer. Regeneration of the polymer allowed essentially 100% HF recovery using heated nitrogen back flow.

EXAMPLE 3

A liquid mixture of 9.6 wt. % of HF in propane was passed through the Nafion ® polymer packed column described in Example 1. During this run, the pressure was maintained at 120 psig (696 cm Hg), temperature at 23° C. and flow was maintained constant at 150 mL/min. The concentration of hydrogen fluoride in the collected product was reduced from 9.6 wt. % to below 900 ppm as determined by the use of a specific ion electrode in an acetate buffer. Regeneration of the polymer allowed essentially 100% HF recovery using heated nitrogen back flow.

I claim:

1. A process for separating HF from organics comprising the step of:

passing a mixture of HF and organics through beads of a fluorinated polymer having at least one sulfonic acid group and, thereafter, isolating the organic from the beads to produce an organic with reduced HF content of about 1 ppm to about 900 ppm.

2. The process of claim 1 wherein the mixture of HF and organics is an azeotropic or azeotrope-like mixture.

3. The process of claim 1 wherein the mixture of HF and organics is at least partly in liquid form.

4. The process of claim 1 wherein the HF and organics mixture is at least partly in gaseous form.

5. The process of claim 1 wherein the organics are selected from a group of chlorofluorocarbons, hydrochlorofluorocarbons, hydrofluorocarbons, and perfluorocarbons.

6. The process of claim 1 wherein the organic is selected from chlorodifluoromethane and difluoromethane.

7. The process of claim 1 wherein the organic is a mixture of 2-chloro- 1,1,1,2-tetrafluoroethane and 1,1,1,2-tetrafluoroethane.

8. The process of claim 1 wherein the organic is a mixture of 2-chloro-1,1,1,2-tetrafluoroethane and pentafluoroethane.

9. The process of either claim 1, 2, 3, 4, 5, 6, 7, or 8 wherein said reduced HF content is about 1 to about 7 ppm.

* * * * *